United States Patent [19]

Gambale

[11] Patent Number: 5,425,709
[45] Date of Patent: Jun. 20, 1995

[54] SHEATH FOR A BALLOON CATHETER

[75] Inventor: Richard A. Gambale, Tyngsboro, Mass.

[73] Assignee: C. R. Bard, Inc., Murray Hill, N.J.

[21] Appl. No.: 96,638

[22] Filed: Jul. 22, 1993

[51] Int. Cl.⁶ .............................................. A61M 25/00
[52] U.S. Cl. ...................................... 604/96; 606/195
[58] Field of Search ................ 604/96, 101, 102, 103, 604/280, 282, 264, 265; 606/194, 192, 191, 195

[56] References Cited

U.S. PATENT DOCUMENTS

| | | | |
|---|---|---|---|
| 4,417,576 | 11/1983 | Baran | 604/101 X |
| 4,423,725 | 1/1984 | Baran | 604/101 X |
| 4,744,366 | 5/1988 | Jang | 604/101 X |
| 5,116,318 | 5/1992 | Hillstead | 606/195 |
| 5,226,889 | 7/1993 | Sheiban | 604/101 |

*Primary Examiner*—John D. Yasko
*Attorney, Agent, or Firm*—Darby & Darby

[57] ABSTRACT

A sheath for a balloon dilatation catheter has a distal guide spring, a proximal tubular shaft, and an expandable portion connected to and between the guide spring and the shaft. The sheath is advanced by pushing a core wire connected inside of the sheath to the distal spring guide. This wire is removable to permit the surgeon to select a variety of wires of different stiffness even while positioning the sheath. When the sheath is positioned at the lesion or stenosis, the wire is removed. A single lumen balloon catheter is then pushed through the sheath using the same or another stiffening wire until the balloon portion of a catheter is within the expandable portion of the sheath. Another version of the invention encloses the distal end of the sheath with material and eliminates the distal spring guide. A conventional guide wire may be inserted and used to position the sheath. A third version includes a sheath with a permanently affixed guide wire which allows a standard dual lumen angioplasty catheter to be positioned using an over-the-wire type method. All versions completely isolate the catheter and guide wire from the patient's bodily fluids. This allows reuse of the catheter and the stiffening wire because re-sterilizing the instruments is less troublesome and protects the patient in the event that the balloon or wire ruptures. All three versions allow rapid wire and/or catheter exchanges without the exchanged instruments contacting the patient's blood vessels. All versions of the invention may be modified to have a perfusion device comprising a plurality of tubes across the expandable portion. These tubes are open at both ends and have side holes so that blood may flow beyond the balloon catheter even when it is inflated.

21 Claims, 5 Drawing Sheets

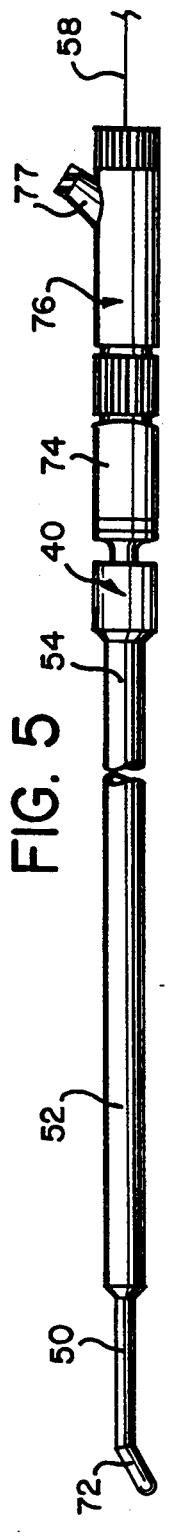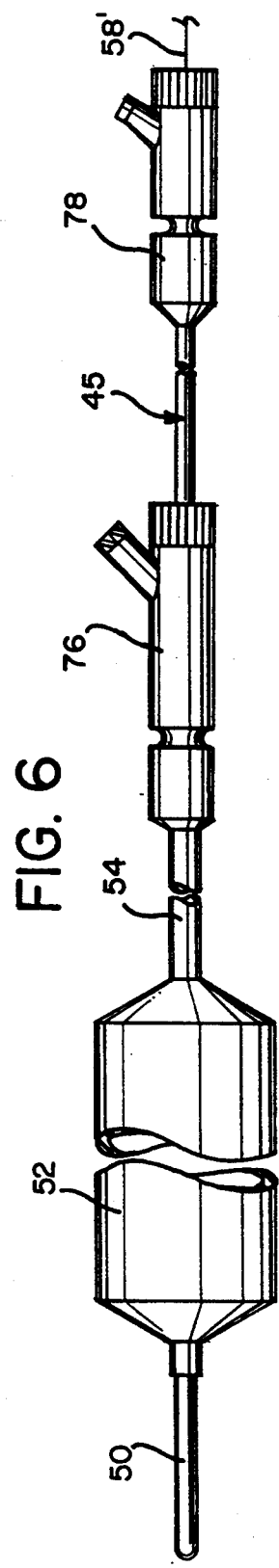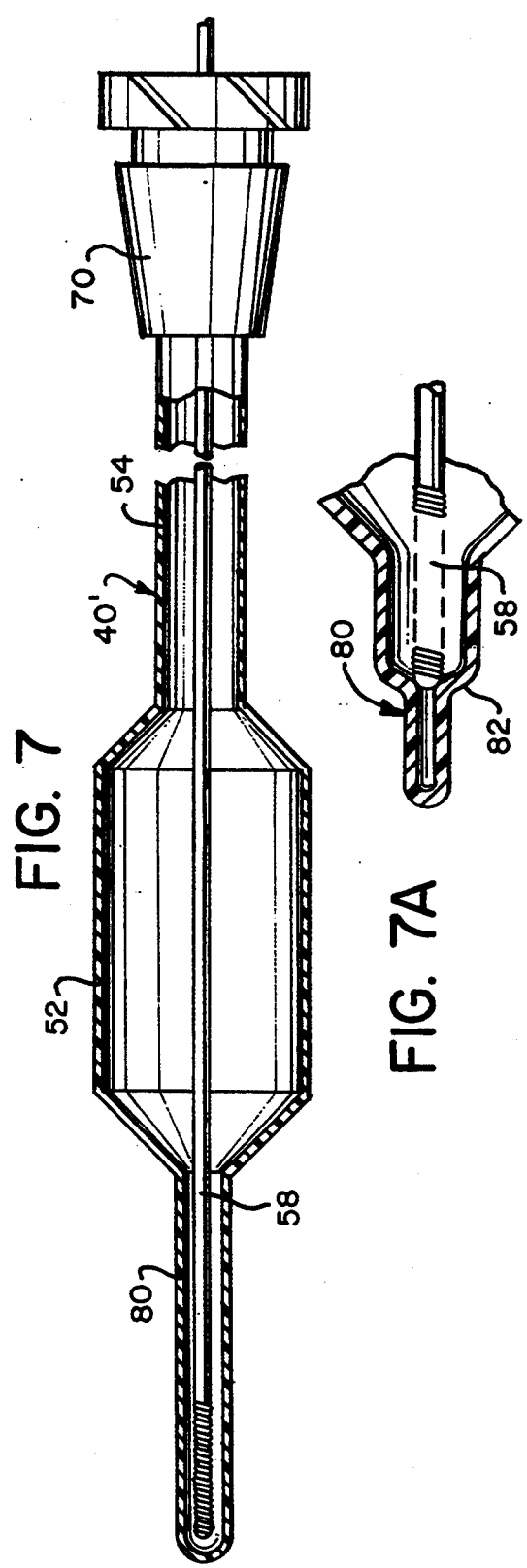

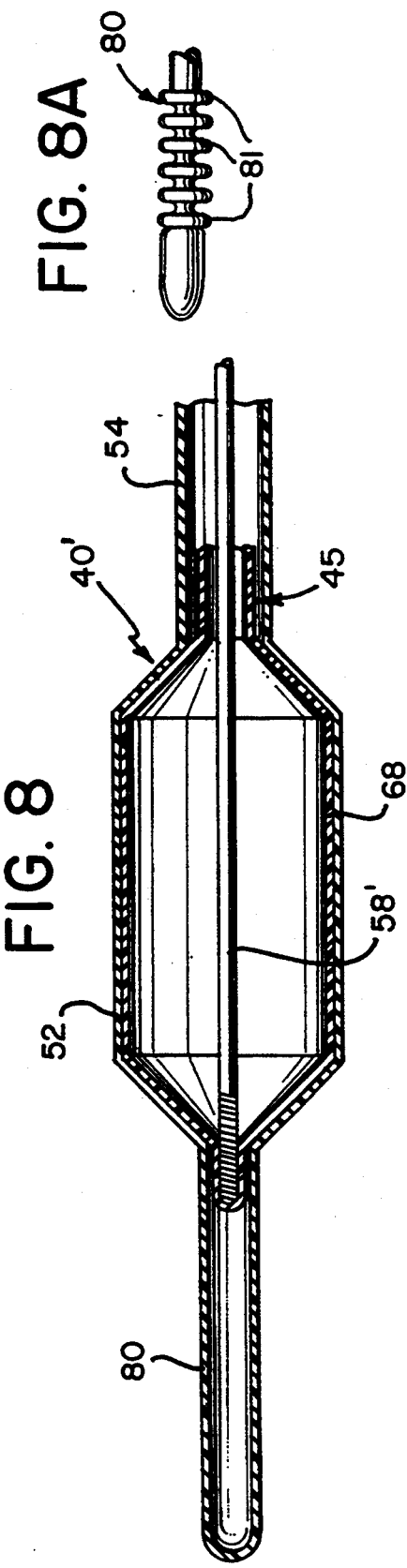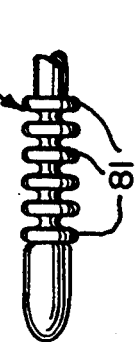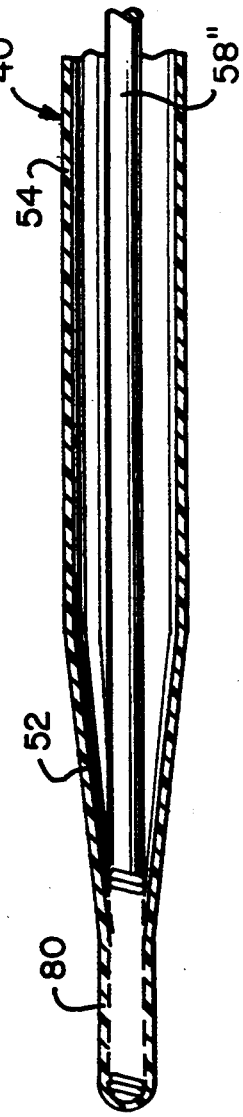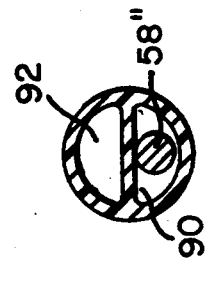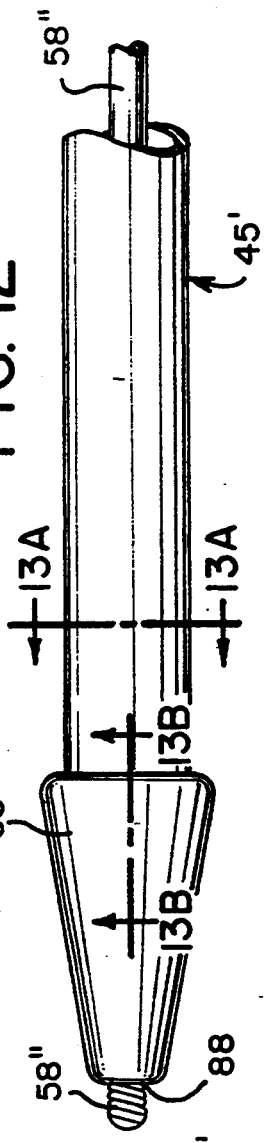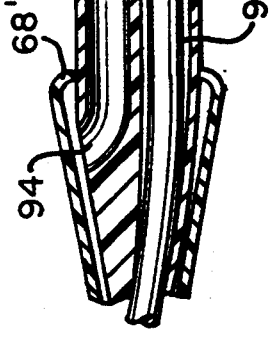

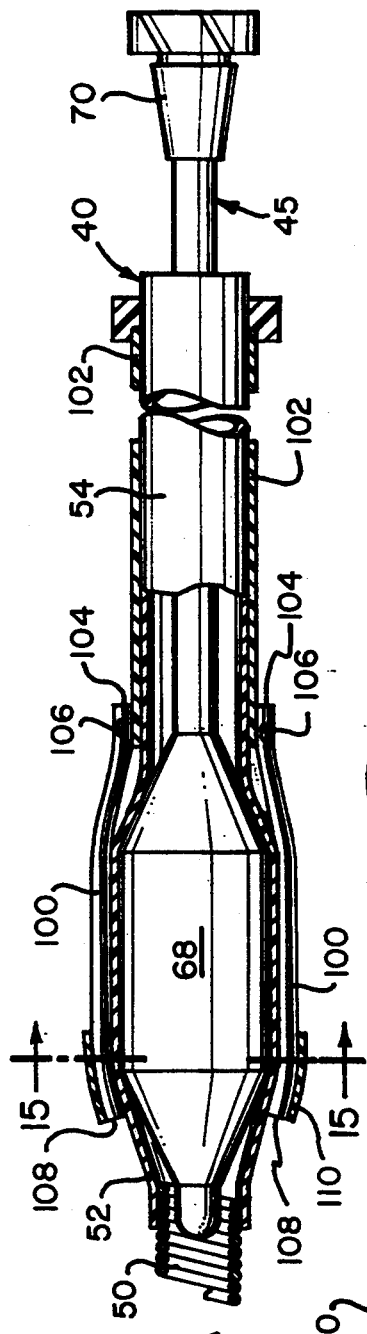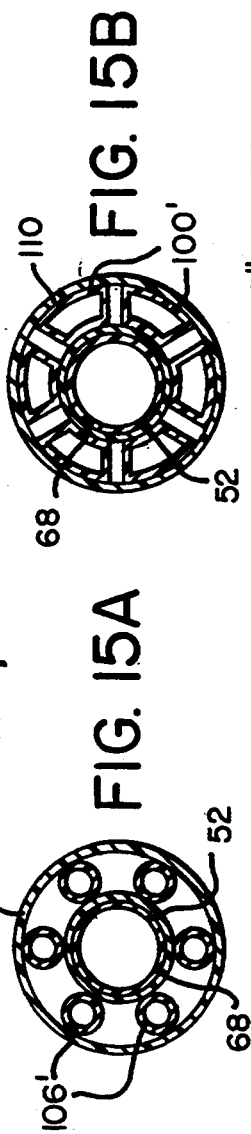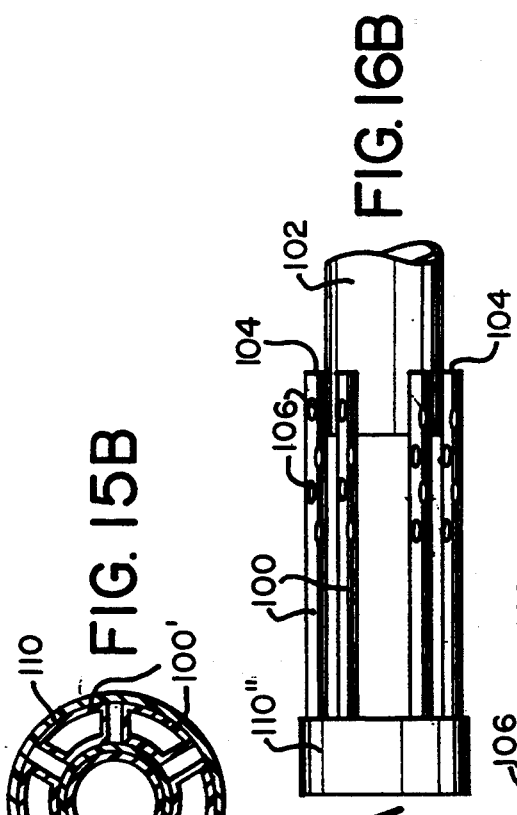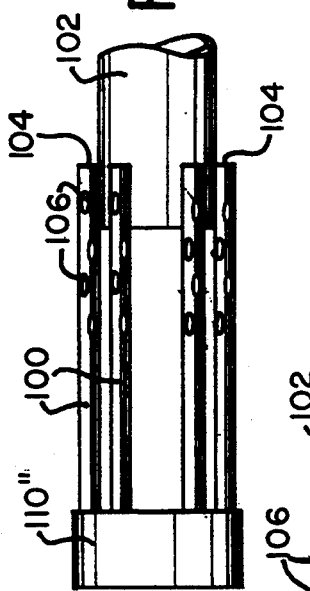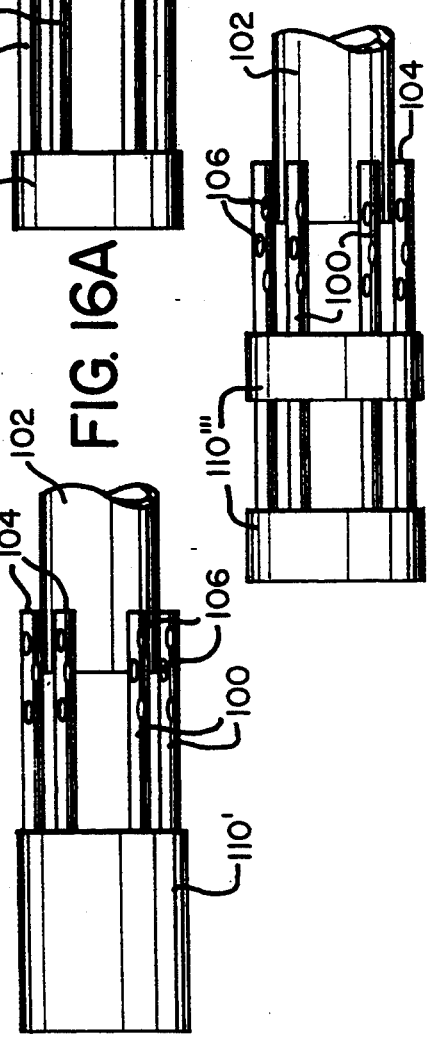

SHEATH FOR A BALLOON CATHETER

FIELD OF THE INVENTION

The present invention relates to a sheath for a balloon catheter, and more particularly, to a sheath allowing rapid wire and catheter exchanges, having an expandable section for covering the balloon portion of the catheter during inflation, and preventing contamination of the catheter and wire with the patient's bodily fluids.

BACKGROUND OF THE INVENTION

Angioplasty balloon catheters and their methods of use are well known. For example, U.S. Pat. No. 5,035,686 to Crittenden and U.S. Pat. No. 4,976,689 to Buchbinder et al. provide general descriptions of angioplasty balloon catheters and their methods of use. The contents of these patents are incorporated herein by reference. Typically, an angioplasty balloon catheter is positioned at a lesion or stenosis in a blood vessel by locating a guide wire at the proper position and then pushing the catheter over the wire. Such a system is commonly referred to as an "over-the-wire" system. The over-the-wire system is desirable because it is relatively easy to push the catheter along the wire to the proper location. However, the over-the-wire system has several drawbacks.

The over-the-wire system does not protect the patient in the event that the balloon ruptures. Should the balloon rupture, pieces of the balloon or the liquid used to inflate the balloon may injure the patient. The over-the-wire system exposes both the catheter and the guide wire to the patient's blood and body fluid thus making reuse of the relatively expensive balloon catheter and wire impractical because of the prohibitive time and cost of re-sterilizing the contaminated instruments. The over-the-wire system does not allow the surgeon to ascertain whether or not the lesion can be penetrated by the balloon until after the costly sterile tray has been opened, sometimes resulting in unnecessary expense. The over-the-wire system does not allow for the rapid exchange of catheters or wires should the surgeon find that a different size or stiffness is required. Also, the over-the-wire system typically requires the guide wire to remain in place during the procedure. The wire must be withdrawn for the surgeon to fluoroscopically "see" the lesion or stenosis. Moreover, such exchanges or withdrawals may be injurious to the patient because of the increased possibility that the patient's artery will be perforated or damaged by repeatedly inserting and removing instruments that directly contact the blood vessel. Damage to the blood vessel walls may result in a thrombus formation, or clot, which is dangerous or even fatal to the patient.

Certain angioplasty balloon catheter systems provide for an exchange of guide wires and balloon catheters. Such exchanges typically require additional instruments such as a wire extension or wire restraining system which requires two persons to operate. Also, catheters are typically manufactured to accommodate only a particular manufacturer's wire, thus sometimes making an exchange impossible if that manufacturer does not make a particular wire or if one is not on hand. These exchanges are often time consuming, an undesirable characteristic of any surgical instrument. Also, the prior art rapid exchange devices have eccentrically located guide wires, thus having inferior control and pushability.

U.S. Pat. No. 5,201,756 to Horzewski et al. discloses a catheter sheath made of a radially expandable material. This sheath is an over-the-wire device which may accommodate a variety of different sized catheters. It does not overcome the problems of the prior art. U.S. Pat. No. 5,219,335 to Willard et al. discloses an over-the-wire introducer sheath and a balloon catheter. The balloon catheter has perfusion openings which allow blood to flow distally of the catheter, but also exposes the catheter to the patient's blood.

U.S. Pat. Nos. 4,976,689 to Buchbinder et al., and 4,327,709 to Hansen et al. disclose sheaths for balloon catheters. However, neither sheath protects the patient from balloon rupture, nor prevents the catheter and wire from contamination, nor prevents damage to the artery walls due to wire and/or catheter exchanges. The sheath of the Buchbinder et al. patent may also operate as a perfusion device, but permits the patient's blood and other bodily fluids to contaminate the catheter and guide wire.

U.S. Pat. No. 4,646,722 to Silverstein et al. discloses a protective sheath for an endoscope allowing for the reuse of the scope. This sheath does not allow for the rapid exchange of catheters or wires, does not allow for the inflation of a balloon catheter, and must be preloaded on the scope before use.

It would therefore be desirable to provide a system which would overcome the drawbacks of these prior art systems.

SUMMARY OF THE INVENTION

The present invention is directed to a sheath for a balloon catheter which isolates the catheter and the wire from the patient's blood vessels and body fluids, while allowing for rapid catheter and wire exchanges, and allowing the balloon portion of the catheter to inflate within the sheath. A perfusion device for use with the sheath or any dilatation device is also disclosed.

One embodiment of the present invention comprises a sheath having a distal spring with a socket connection at its proximal end for receiving a stiffening (or core or guide) wire. The stiffening wire may be removed at the socket connection and replaced with another, permitting the surgeon to select a variety of wires of different sizes and stiffness. The sheath has an expandable section located just proximal the distal spring. The proximal end of the expandable portion is connected to a shaft. The socket connection seals the expandable portion so that blood does not enter the interior of the expandable portion or shaft, and thus does not contact the catheter or wire. The sheath is positioned at the lesion or stenosis and the wire is removed. The same or a different wire is loaded into the catheter and is used to push the balloon catheter through the sheath. If either the wire or the catheter needs to be exchanged during the procedure, it may be done quickly and safely inside the sheath without contacting the patient's artery walls and without moving the sheath. When the balloon catheter is properly positioned, the wire is preferably removed and the balloon inflated. The sheath's expandable section will expand with the balloon. Because the catheter and wire do not contact patient's blood, the instruments are easily re-sterilized and may be reused.

A second embodiment of the present invention comprises a sheath wherein the distal end of the sheath is enclosed with suitable material. This enclosed tip may receive a standard guide wire; thus the distal spring segment of the first embodiment is unnecessary in favor of the removable guide wire. The tip may be designed to accept guide wires from different manufacturers. This embodiment may also allow the reuse of the catheter and the wire, because the sheath is completely enclosed and does not contact the patient's blood or other bodily fluids.

The sheath according to the embodiments of the present invention may be used in the following manner. A stiffening wire is pre-loaded into the sheath and, using the wire to steer and push, the sheath is positioned so that the expandable portion is across the lesion or stenosis. If a wire having a different stiffness is desired, it is quickly and easily replaced by removing the wire and inserting another. This can be performed by one person. Once the sheath is properly positioned, the wire is withdrawn and may be placed in a balloon catheter (or another wire may be used). The catheter is preferably a low profile, single lumen balloon catheter. A single lumen balloon catheter offers the following advantages: low profile; simplistic design; and faster inflation/deflation and enhanced flexibility due to the single, large, round lumen. Balloon catheters having extremely low profiles are possible due to the single lumen catheter. The single lumen balloon does not require a separate guide wire lumen to extend through the balloon, so the shaft can terminate at the proximal end of the balloon portion, and the balloon can wrap around the wire. The balloon catheter is placed inside the sheath and pushed with the guide wire until it is properly positioned across the lesion or stenosis. The sheath's expandable section may be partially inflated to pre-dilate the lesion or stenosis, thus easing the balloon catheter positioning. Because the distal end of the sheath is pushed by the wire, the balloon itself is never pushed into the lesion, but rather, it is pulled forward by the advancing tip, thus the balloon is more easily positioned.

A preferred embodiment may include a fluoroscopically opaque band on the catheter balloon to allow the surgeon to "view" the catheter after the wire is removed. An opaque band may also be included on the expandable portion of sheath to assess the position of the balloon catheter in relation to the sheath. With the present invention, fluoroscopic assessment of the lesion does not require the dangerous practice of removing and replacing the wire, because the wire has already been removed. Once the catheter is in position, the wire is preferably removed and the balloon is inflated. Even if the surgeon elects to maintain the guide wire in the catheter during inflation, the danger of withdrawing the wire is greatly reduced because the wire does not contact the patient's blood vessels. The sheath may be repositioned by replacing the wire and relocating the sheath to the desired location. When the procedure is complete, the catheter and sheath are removed from the patient together.

A third embodiment may include a guide wire permanently attached to the distal end of the sheath. This allows a conventional, double lumen balloon catheter to be positioned within the sheath using an over-the-wire type method. However, the low profile and single lumen catheter advantages described above are sacrificed.

The catheter sheath protects the patient in the event that the balloon ruptures, and also allows for rapid exchanges of balloons should the surgeon determine that a larger or smaller diameter balloon is desirable. Also, the balloon catheter is not exposed to the patient's blood, and therefore, may be reusable. Finally, the lesion or stenosis can be accessed if the surgeon has difficulty positioning the guide wire/sheath. Thus, the desired balloon catheter size can be selected, or the procedure may be abandoned, before the sterile tray of an unneeded balloon catheter is opened. This saves the expense of wasting the relatively costly balloon catheter.

A modification of the above embodiments may include a perfusion device having a plurality of tubes connected to a second sheath. The sheath is slightly shorter than the catheter or catheter sheath, and the tubes are attached to the distal end of the sheath. The tubes are approximately the length of the inflatable or expandable portion. The tubes have openings at their proximal and distal ends and may also have a plurality of side holes. The distal end of the tubes are secured by an elastic membrane. This membrane retains the co-linearity of the tubes and makes the distal end of the sheath (or catheter) and perfusion device combination less traumatic by eliminating the uneven surface caused by the tubes.

The perfusion device is pre-loaded onto a catheter or sheath, with the distal end of the tubes being positioned slightly proximal to the inflatable portion and the proximal end of the perfusion device sheath being positioned very close to the proximal end of the catheter or catheter sheath, extending out of the patient. Once the lesion or stenosis is sufficiently dilated to accept the additional diameter of the perfusion device tubes, the catheter balloon is deflated, and the surgeon slides the perfusion device sheath forward so that the tubes extend slightly beyond the inflated portion of the catheter or sheath. The balloon is reinflated and the tubes allow blood to flow beyond the stenosis and catheter.

This catheter/sheath system has the advantages of the "pushability" of the over-the-wire systems as opposed to the rapid exchange type devices which have eccentrically located guide wires. This invention has the control and pushability advantages of a coaxial catheter system, but optimizes this feature by having only one lumen. The present invention has these advantages while avoiding the drawbacks of the over-the-wire system.

BRIEF DESCRIPTION OF THE DRAWINGS

The foregoing and other features of the present invention will be more readily apparent from the following detailed description and drawings of an illustrated embodiment in which:

FIG. 5 is a side elevational view of a sheath with a luer fitting according to the present invention having a guide wire inserted, and a Touhy-Bourst and Y-body fittings installed;

FIG. 6 is a side elevational view of a sheath according to the present invention having an inflated balloon catheter positioned within it;

FIG. 7 is a partial cross-section of a second embodiment of the present invention;

FIG. 7A is a partial cross-sectional view of a modification of the second embodiment of the present invention;

FIG. 8 is a cross-section of the sheath shown in FIG. 7, having a balloon catheter and catheter stiffening wire positioned within it;

FIG. 8A is a partial side elevational view showing the tip of the second embodiment of the present invention;

FIG. 11 is a partial cross-section of a third embodiment of the sheath according to the present invention;

FIG. 12 is a side elevational view of a dual-lumen balloon catheter for use with the sheath of FIG. 11;

FIG. 13A is a cross-section of the catheter of FIG. 12, taken along lines 13A—13A;

FIG. 13B is a cross-section of the catheter of FIG. 12, taken along lines 13B—13B;

FIG. 14A is a partial cross-section of a portion of a sheath according to the present invention having an inflated balloon catheter within it and having a perfusion device attached thereto;

FIG. 15A is a cross-section of the sheath of FIG. 14A taken along lines 15—15, showing another embodiment of the perfusion device;

FIG. 15B is a cross-section of the sheath of FIG. 14A, taken along lines 15—15, showing another embodiment of the perfusion device;

FIGS. 16A-16C; are partial side elevational views of three embodiments of the perfusion device;

DESCRIPTION OF THE PREFERRED EMBODIMENTS

Figure 1:
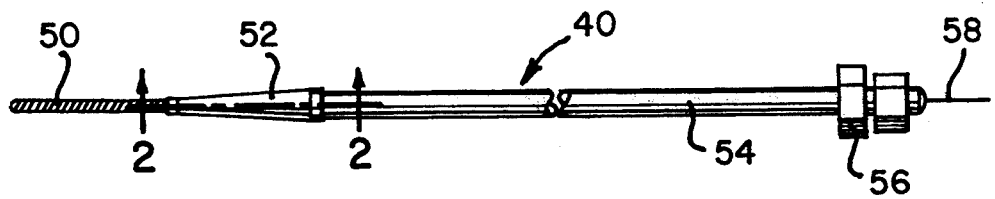
FIG. 1 is a side elevational view of one embodiment of the present invention.
Figure 3:
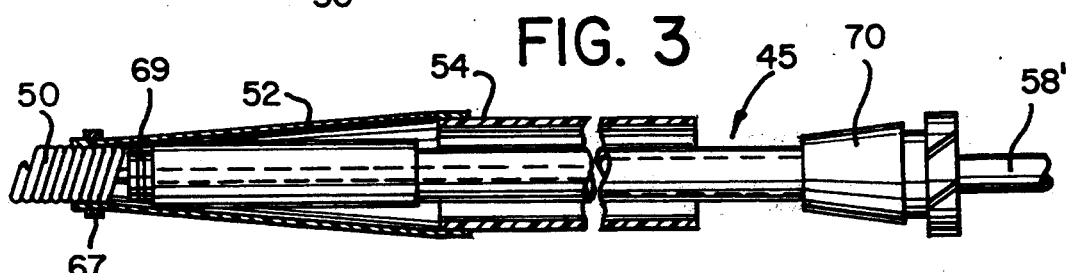
FIG. 3 is a partial cross-section of the sheath of FIG. 1, the sheath having a balloon catheter positioned within it.
Figure 9:
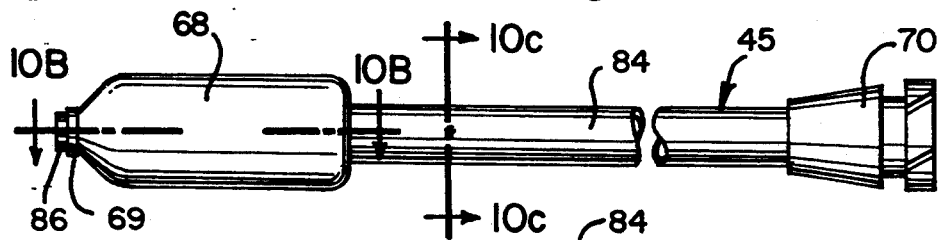
FIG. 9 is a side elevational view of a single lumen balloon catheter for use with the sheath of the present invention.

FIG. 1 shows one embodiment of the balloon catheter sheath 40 of the present invention. At the distal end of the sheath is a spring guide 50 for aiding in the steering and placement of the sheath within the patient in a conventional manner. This spring guide 50 may be made of any suitable metal or plastic coil, for example, stainless steel or platinum alloy to achieve the desired flexibility, strength, and opacity. In a preferred embodiment of the present invention, this spring guide 50 is approximately three centimeters long. An expandable portion 52 is secured to the guide spring. This expandable portion 52 may preferably be made of polyethylene, polyvinylchloride (PVC) or polyethylene terephthalate (PET), a material manufactured by DuPont and others. The expandable section is preferably made of PET because it offers low profile, bondability, and strength advantages over the other materials and is approximately 5 cm long. The expandable section is manufactured by extruding and blow molding the material in a conventional manner. Alternatively, the expandable segment may be a wire braid made of plastic, or plastic-coated metallic wire, which has enhanced torque advantages. The plastic braid may be made of polyetheretherketone and the metallic braid may be urethane coated stainless steel or platinum alloy. The braid may expand by contacting the inflated balloon or by pulling an integral pull-wire. The expandable portion 52 is attached at its proximal end to a shaft 54, preferably a single lumen tube. The shaft 54 may be made of any suitable biocompatible, lubricous material, such as are typically used for catheters and the like, such as TEFLON, PVC, polyimide, or, in a preferred embodiment, polyethylene. The shaft is manufactured in the conventional manner for example by extruding the material. The material may also undergo additional stretching to achieve the desired wall thickness. At the proximal end of the shaft 54 is a removable compression fitting 56 or permanently attached luer. The internal diameter of the expandable portion 52 and the single lumen tube 54 are sufficient to accommodate a balloon catheter, preferably a single lumen balloon catheter as shown in FIGS. 3, 8, and 9. A preferred embodiment of the sheath can accommodate a straight or tapered balloon of up to 4 mm in diameter and 40 mm in length. A removable stiffening wire 58 is selectively insertable into the sheath to provide additional stiffness and held in place by the compression fitting 56.

Figure 2:
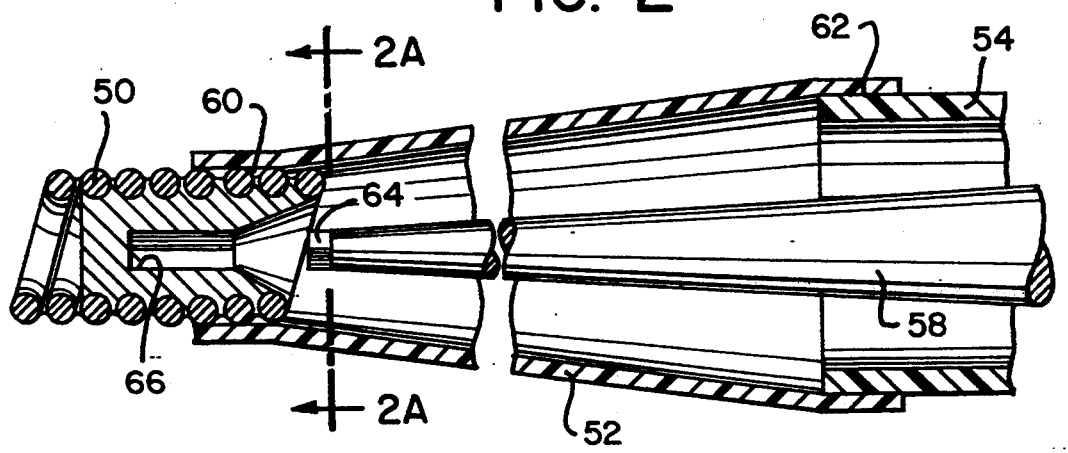
FIG. 2 is a cross-section of the sheath of FIG. 1, taken along lines 2—2.
Figure 2A:
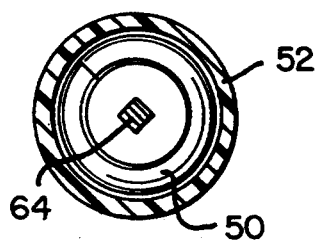
FIG. 2A is a cross-section of the sheath of FIG. 2, taken along lines 2A—2A.

FIG. 2 is a cross sectional view of a portion of the catheter shown in FIG. 1. In the embodiment of FIGS. 1 and 2, the expandable portion 52 is bonded to the guide spring 50 at location 60 and to the single lumen tube 54 at location 62. The expandable section is bonded by any conventional method known in the art, such as epoxies, cyanoacrylate, or thermal bonding. The stiffening wire 58 is removable, thus allowing the selection of any of a range of wires providing the appropriate stiffness necessary to properly place the sheath across the lesion or stenosis. Alternatively, a telescoping technique may be used to alter the stiffness within the sheath. That is, a tube is slid distally over the wire to increase stiffness. Because the stiffening or core wire 58 is removable, the wire's 58 distal end has a tip 64 which is received by a socket 66 located at the proximal end of the guide spring 50. The tip 64 preferably has a custom-made complementary-shaped tip to be securely received by the socket, as shown in FIGS. 2 and 2A. The socket 66 is created when the spring guide 50 is soldered or brazed by inserting a mandrel which does not "wet". When the mandrel is removed, the cavity formed is the socket 66. The socket connection seals the expandable portion 52 so that blood or other bodily fluids do not contact or contaminate the catheter or wire. This sealed sheath simplifies the re-sterilization process, allowing the catheter 45 and wire 58 to be reused. Once the sheath is properly placed along the lesion or stenosis, the stiffening wire 58 is removed by loosening the compression device and pulling it out. Once positioned, the expandable portion 52 may also serve as an initial dilatation device when inflated through a Y-body 76, as shown in FIG. 5.

Figure 4:
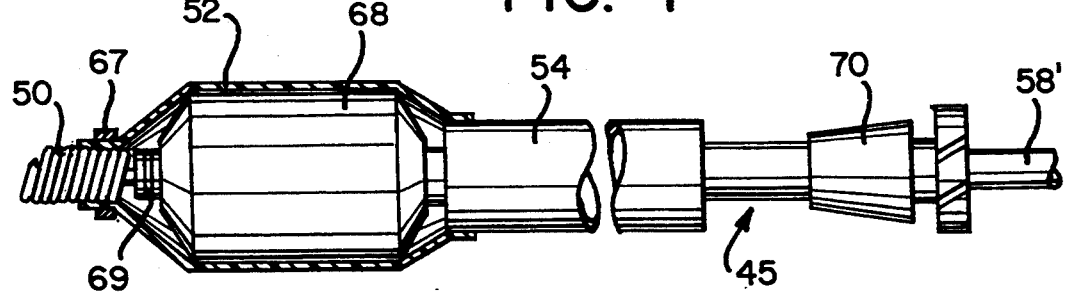
FIG. 4 is a partial cross-section of the sheath shown in FIG. 3 with the balloon catheter inflated.

The stiffening wire 58, or any suitable wire, is placed within a desired balloon catheter for added "pushability". The surgeon may wish to use the proximal end, rather than the distal end, of the wire 58 for added stiffness, because of the thicker, untapered proximal end and to keep the wire's complementary-shaped tip 64 from damaging the balloon catheter. Alternatively, the wire can be manufactured with tapers at both ends. One taper has the complementary-shaped tip 64 and the other is tapered to optimize balloon placement. The catheter 45 is then inserted into the sheath 40 and advanced until the balloon portion of the catheter 68 is within the expandable portion 54 of the sheath as may be indicated fluoroscopically by radiopaque markers 67,69 on the sheath, catheter, and wire (which is made of radiopaque material). The radiopaque markers 67,69 on the sheath and catheter are very thin bands (preferably on the order of 0.0001") of suitable radiopaque material such as platinum or tantalum which is bonded to the sheath or catheter with an adhesive such as cyanoacrylate. FIG. 3 shows the catheter 45 properly placed within the sheath 40. The catheter luer 70 and catheter guide wire 58' are also shown. FIG. 4 shows the balloon 68 inflated within the sheath 40. The wire 58 is shown in dashed lines. Preferably, the wire is removed before the balloon catheter is inflated. The expandable portion 52 of the sheath expands with the inflation of the balloon 68. The radiopaque marker 69 on the balloon catheter 45 allows the surgeon to "view" the catheter once the wire is removed. Also, the present invention allows fluoroscopic assessment of the lesion without repeated withdrawals of the guide wire because it is preferably removed prior to inflation of the balloon catheter. Even if the surgeon elects to maintain the guide wire in the catheter during inflation, the danger of withdrawing the wire is greatly reduced because the wire does not contact the patient's blood vessels.

FIG. 5 shows the sheath 40 with a stiffening wire 58 inserted. The distal spring guide 50 has a "J" tip 72 to aid in steering the sheath into position. Other conventionally known methods for steering the catheter may also be used. This figure shows the wire 58 connected to the sheath with a straight Touhy-Bourst compression device 74. A Touhy-Bourst compression device 74 has a threaded cap which causes a radial decrease with a longitudinal compression of an internal silicone sleeve and may be used instead of a conventional steering handle when positioning the sheath 40. The Touhy-Bourst device 74 is connected to a Y-body 76. The Y-body 76 has a Y-leg 77 through which a vacuum may be applied to retain the expandable portion 52 in a low profile.

FIG. 6 shows a balloon catheter 45 in place within the sheath 40. The stiffening wire 58' is in place within the catheter (it may be the same or a different wire than used to position the sheath 40). Preferably, the wire 58' should be removed during inflation. An inflation device is connected to the single lumen balloon catheter 45 via a second Y-body 78. The balloon 68 (enclosed within the sheath) is inflated and the expandable portion 52 of the sheath 40 expands with the balloon.

FIGS. 7 and 8 show a second embodiment of the present invention. FIG. 7 shows a cross-sectional view of this second embodiment. This differs from the first embodiment because distal tip 80 comprises material enclosing the distal end of the sheath. The tip's 80 wall thickness is preferably extremely thin, for example, on the order of tenths of thousandths of an inch and, in a preferred embodiment, on the order of 0.0002". This prevents compromising the flexibility and stiffness properties of a guide wire 58. Although compliant materials such as latex, surlyn, manufactured by DuPont and kraton maybe used to form the tip, these materials will allow some axial distention, and may have too large a profile to be practical. Highly oriented materials such as oriented PET provide very thin walls and satisfactory axial and radial strength, but tend to be stiff. The preferred design is an oriented material such as PET having radial corrugations 81 as shown in FIG. 8A. Oriented (pre-stretched) PET having the radial corrugations 81 shown in FIG. 8A provides the longitudinal strength and flexibility required to achieve the wall thickness and flexibility requirements. This corrugated tip is formed in a mold or by axially collapsing the tube. In a preferred embodiment, the radial corrugations 81 extend no more than 0.001" above the profile of the rest of the distal tip 80. The oriented PET is prepared so that it will not inflate with the expandable portion. The sheath may be pre-curved to have the "J" shape, but such a pre-bent sheath may resist straightening.

The distal tip 80 maintains total isolation of the instruments and the external fluids. This closed sheath completely encloses the balloon catheter 45 (shown in FIG. 8) and permits a removable guide wire 58, such as any commercially available angioplasty guide wire, to be inserted into the sheath's tip 80. Thus, the unique spring guide 50 having the socket 66 of the first embodiment is unnecessary. The distal tip 80 and the guide wire 58 act in unison to allow the sheath to be conventionally steered. As shown in FIG. 7A, additional interfacial shoulders 82 may be included to aid in pushing or pulling the sheath across the lesion or stenosis as the guide wire is advanced. That is, a shoulder 82 is provided to seat the guide wire tip should the tip not fit into the distal end of the sheath. This embodiment of the present invention is completely enclosed and prevents contamination of the balloon catheter and guide wire with the patient's blood and other body fluids, thus greatly simplifying the instruments' cleanup, thus allowing reuse.

Figure 10B:
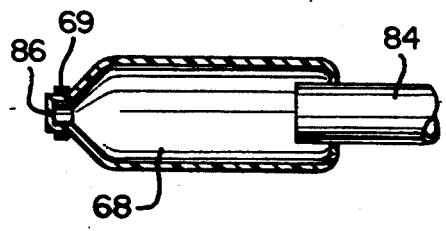
FIG. 10B is a cross-section of the catheter of FIG. 9, taken along lines 10B—10B.
Figure 10A:
FIG. 10A is a cross-section of the catheter of FIG. 9, taken along lines 10A—10A.
Figure 10C:
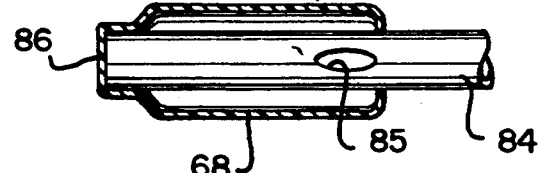
FIG. 10C is a cross-section of the catheter of FIG. 9, taken along lines 10B—10B, showing another embodiment of the catheter.
Figure 14B:
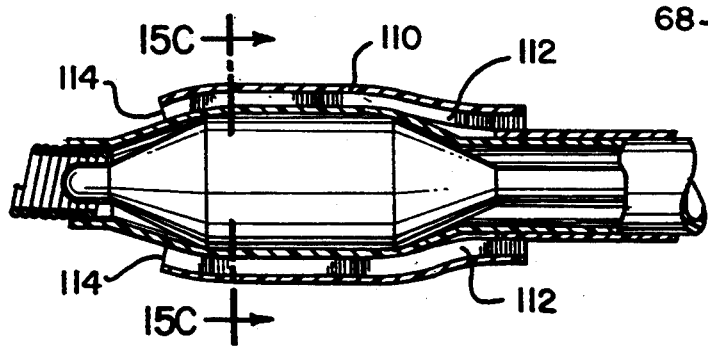
FIG. 14B is a partial cross-section of a portion of a sheath according to the present invention having an inflated balloon catheter within it and having another embodiment of the perfusion device attached thereof.
Figure 15C:
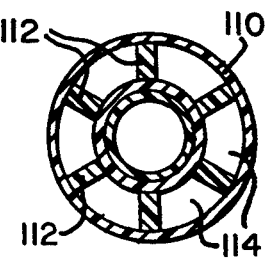
FIG. 15C is a cross-sectional view of the sheath of FIG. 14B, taken along lines 15C—15C.

The catheter used with the sheath 40 is preferably a low profile single lumen balloon catheter, as shown in FIGS. 3 and 8. A single lumen balloon catheter has several advantages: low profile; simplistic design; and faster inflation/deflation and enhanced flexibility due to the single, large, round lumen. Balloon catheters having extremely low profiles are possible due to the single lumen catheter. The single lumen balloon does not require a separate guide wire lumen to extend through the balloon, so the shaft can terminate at the proximal end of the balloon portion, and the balloon can wrap around the wire. The single lumen balloon catheter 45 is shown is more detail in FIGS. 9, 10A and 10B. The balloon catheter 45 has a flexible shaft 84 which is connected at its distal end to a balloon portion 68 and terminates at the proximal end of the catheter. The shaft has a single, large lumen 86 which runs the length of the catheter 45 and is closed at the catheter's distal tip 88. Because the single lumen catheter does not contact the patient's circulatory system, the shaft 84 may be made of any suitable non-compliant, flexible material, such as extruded polyethlene. The cross-section shown in FIG. 10A shows the large, single lumen 86. The cross-section shown in FIG. 10B shows that the shaft 84 terminates near the proximal end of the balloon portion 68. The distal tip 86 is connected to the distal end of the balloon portion. Alternatively, as shown in FIG. 10C, the shaft 84 can extend through the balloon and have a port 85 to allow inflation. This will not allow the extremely low profile catheter. The interfacial shoulders discussed above may also be used in the single lumen balloon catheter to properly seat the guide wire.

FIGS. 11, 12, 13A and 13B disclose a third embodiment of the present invention. FIG. 11 shows a cross-sectional view of a third embodiment of the sheath 40". The sheath has a permanently attached guide wire 58". This permanently attached guide wire 58" allows a conventional dual lumen angioplasty catheter to be inserted into the sheath 40" in an over-the-wire like manner. FIG. 12 is a side view of a typical dual lumen angioplasty catheter 45' having a separate inflatable portion 68' and a distal opening 88 which receives a guide wire 58" in order to advance the catheter 45'. FIG. 13A shows a cross-section of the dual lumen portion of the catheter. A first lumen 90 receives the guide wire 58", a second lumen 92 allows the inflation liquid to be transported to the balloon portion 68'. FIG. 13B shows a side cross-sectional view of the dual lumen catheter. The second lumen 92 terminates at an inflation port 94 which permits the inflation fluid to expand the balloon portion 68'.

The sheath according to the first and second embodiments is used in a dilatation procedure as follows: a stiffening or core wire 58 is pre-loaded into the sheath; the sheath is pulled taught so that it hugs the wire, maintaining the compressed profile of the expandable portion; the shaft is locked to the wire using a compression device, such as a Touhy-Bourst type device. A vacuum is applied to the sheath through a Y-body in series with a Touhy-Bourst or other compression fitting to maintain the low profile of the expandable portion 52 (i.e., prevent it from opening or expanding). The device is steered through the circulatory system towards the lesion or stenosis. A "J" tip or other conventional shape may be created with the guide wire 58 tip to assist in steering the sheath 40 into position across the lesion or stenosis. If the surgeon determines that an alternate stiffness is desired, the wire 58 may be removed and replaced with a wire of another thickness or stiffness without further contact against the patient's artery walls. The wire is removed by reducing the vacuum and loosening the compression device 56 from the wire. Positive pressure may be applied, if necessary, to aid in removing the wire. The wire is then withdrawn and another replaced without removing the sheath 40. When positioning the sheath, the surgeon may determine that the lesion or stenosis cannot be penetrated with the originally selected balloon catheter size and may decide to use a smaller balloon catheter or decide to abandon the balloon catheter procedure entirely, before the balloon catheter sterile tray has been opened, thus preventing the unnecessary expense of wasting a balloon catheter. The sheath may be used to pre-dilate the lesion or stenosis before the balloon catheter is inserted into the sheath. The sheath is inflated in the same manner as a balloon catheter: a Y-body (76 in FIGS. 5 and 6) is attached to the compression device 74, tightened onto the wire 58, and inflated through the Y-leg 77 of the Y-body.

Once the sheath is in place, the stiffening or core wire 58 is removed and inserted into the balloon catheter 45. The surgeon may wish to put the proximal end of the stiffening wire into the balloon for additional stiffness and to avoid the complementary-shaped tip, which may damage the balloon catheter. The catheter is easily positioned across the lesion or stenosis by advancing it within the sheath. Because the wire 58 propels the balloon catheter, the balloon portion of the catheter is pulled, rather than pushed, through the stenosis and therefore is more easily positioned. Should the surgeon desire a different sized catheter, the catheters are easily exchanged through the sheath, again without contacting the patient's artery wall. It is also contemplated that the surgeon may preload the catheter into the sheath and simultaneously position both across the stenosis.

The third embodiment is used in a dilatation procedure in a similar manner. The sheath 40" is positioned by advancing it with the permanently affixed wire 58". The dual-lumen catheter 45' is then advanced over the guide wire 58" in the well-known "over-the-wire" method.

If the balloon ruptures during the procedure, even a severe radial fracture would not cause the patient harm because the sheath protects the patient from balloon fragments which may dislodge from the catheter, or the inflation liquid which may escape from the ruptured balloon. The patient is also protected from a rupture of the wire 58. The catheter and wire are not exposed to the patient's bodily fluids and therefore these instruments may be resterilized and reused.

At the completion of the procedure, the sheath and catheter are removed together.

FIGS. 14–18 show a modification of the balloon catheter sheaths described above. This modification is seen in FIG. 14A and is a flow assist perfusion device which allows blood to flow distally of the sheath even when the balloon part 68 of the catheter is inflated and the expandable portion 52 of the sheath is expanded. The device consists of at least one, but preferably a series of tubes 100. The tubes 100 are connected to a second sheath 102 at the proximal end of the tubes 100. The perfusion device sheath 102 allows the tubes to be positioned around the balloon catheter sheath 40. As shown in FIGS. 15A and 15B, these tubes may have either a circular (106' of FIG. 15A) or a rounded trapezoidal-type shape (100' of FIG. 15b). The round profile tubes 100' can withstand greater pressure, but the trapezoidal-type shape 100" optimizes the available space for maximum blood flow. The perfusion device sheath 102 is slightly shorter than the catheter sheath and preferably about 10–20 cm shorter and may be made of, for example TEFLON, PVC, polyimide, or preferably polyethylene and in the same manner as the catheter sheath shaft 54. The tubes 100 are attached to the distal end of the perfusion device sheath, preferably about 1 cm from the distal end of the sheath 102. The tubes 100 are attached to the perfusion device sheath 102 by any conventional method such as with a UV curable adhesive or cyanoacrylate. The tubes 100 are approximately the length of the expandable portion 54 (typically about 5 cm overall). Blood enters these perfusion tubes at proximal openings 104 at the proximal ends of the tubes and/or through side holes 106 positioned at various locations along the tubes. The blood exits the perfusion tubes at terminal openings 108 at the distal end of these tubes. The tubes are covered by at least one elastic membrane 110 which keeps the tubes together during positioning of the sheath and allow for radial expansion when the balloon is inflated. The membrane also makes the distal end less traumatic because it eliminates the uneven surface caused by the tubes and maintains axial alignment. The membrane may be one large membrane 110" extending proximally from the tubes' distal end to a location distal the side holes 106 as shown in FIG. 16A; a single band 110" at the distal end of the tubes as shown in FIG. 16B; or two smaller bands 110" one at the tubes' distal end and the other at a proximal location but distal of the side holes 106 as shown in FIG. 16C. The elastic membrane 110 makes the distal end of the tube/sheath combination less traumatic to the patient by eliminating the uneven surface caused by the tubes and keeps the tubes co-linear. The tubes 100 expand when the catheter is inflated and the expandable portion 54 of the sheath expands. Alternatively, as shown in FIGS. 14B and 15C, the perfusion device can be modified to replace the tubes 100 with a series of rods 112 that are completely covered with the elastic membrane 110 to create channels 114 for blood flow.

Figure 17:
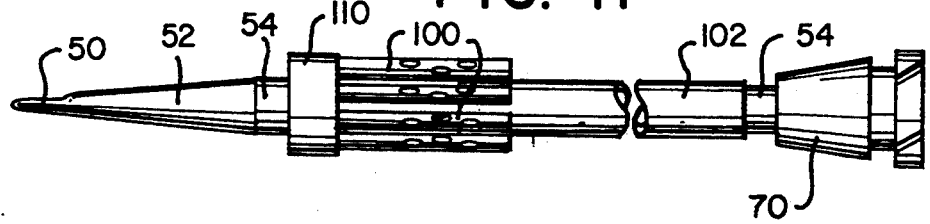
FIG. 17 is a side elevational view of the sheath of the present invention having a preloaded perfusion device in an initial position.
Figure 18:
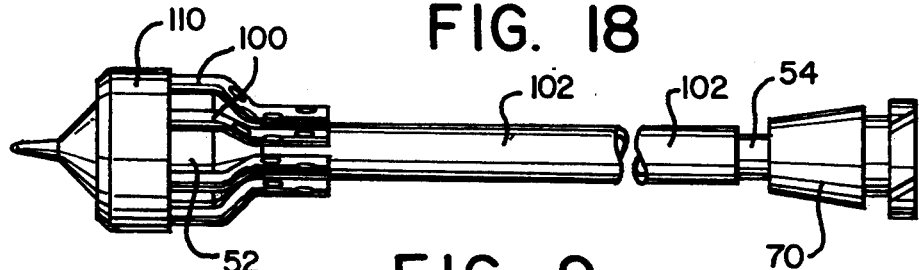
FIG. 18 is a side elevational view of the sheath of the present invention having the perfusion device in place over the expandable portion and the balloon catheter inflated.

The perfusion device is pre-loaded onto the balloon catheter sheath 40 or a balloon catheter 45 before the sheath 40 or catheter 45 is inserted into the patient. The device is initially positioned with the distal end of the tubes 100 located proximally to the expandable portion 54 or the balloon portion 68 of the catheter. The proximal end of the perfusion device is positioned very close to the proximal end of the balloon catheter sheath 40 or catheter 45, so that it extends outside of the patient. This initial position is shown in FIG. 17. When the catheter or sheath is positioned across the lesion or stenosis, the stenosis is enlarged by inflating the balloon catheter. Once the stenosis has been dilated enough so that it can accept the additional diameter of the tubes 100, the balloon portion of the catheter 68 is deflated and the surgeon manually slides the perfusion device sheath 102 distally to position the tubes 100 over the expandable portion 54 of the balloon. When the balloon is reinflated, the perfusion device permits blood to flow beyond the stenosis and inflated balloon. In this position, the distal end of the tubes 100 should be located beyond the expanded portion of the balloon to allow blood to flow beyond the stenosis.

The perfusion tubes allow blood to flow distally of the lesion or stenosis even when the balloon catheter is fully inflated. Thus, the patient's discomfort is reduced even during prolonged dilatation procedures due to improved blood flow through the artery during the procedure. This perfusion device may be used with any inflatable dilatation device that is exposed to the patient's blood vessel.

While the invention has been particularly shown and described with reference to preferred embodiments thereof, it will be understood by those skilled in the art that various changes in form and details may be made therein without departing from the spirit and scope of the invention.

What is claimed is:

1. A stenosis dilatation method, comprising the steps of
    inserting a sheath having a stiffening wire into a patient's circulatory system;
    using the stiffening wire to advance and steer the sheath through the patient's circulatory system;
    positioning an expandable portion of a sheath across the stenosis;
    advancing the balloon catheter through the sheath until an inflatable portion of the balloon catheter is properly positioned across the stenosis and within the expandable portion of the sheath;
    inflating the inflatable portion of the balloon catheter, causing the expandable portion of the sheath to expand;
    deflating the balloon catheter, causing the expandable portion of the sheath to contract; and
    removing the sheath and balloon catheter simultaneously when the stenosis dilatation is completed.

2. The method of claim 1, further comprising the steps of:
    loading the stiffening wire into the sheath before inserting the sheath into the patient;
    removing the stiffening wire from the sheath after the expandable portion of the sheath is positioned across the stenosis; and
    loading one of either the stiffening wire and another wire into the balloon catheter prior to advancing the balloon catheter through the sheath.

3. The method of claim 2, further including the step of removing the loaded wire from the balloon catheter prior to inflating the balloon catheter.

4. The method of claim 1, wherein the step of advancing the balloon catheter comprises pushing the balloon catheter over the stiffening wire in the sheath.

5. The method of claim 2, wherein the step of advancing and steering the sheath further comprises the steps of:
    determining that a different stiffening wire is desired;
    removing the stiffening wire from the sheath without removing the sheath from the patient's circulatory system; and
    loading a second stiffening wire into the sheath without removing the sheath from the patient's circulatory system.

6. The method of claim 2, further comprising the steps of:
    determining that another size balloon catheter is desired after the balloon catheter is positioned across the stenosis;
    replacing the stiffening wire in the balloon catheter;
    removing the balloon catheter from the sheath by pulling the wire;
    loading the stiffening wire in a second balloon catheter; and
    advancing the second balloon catheter through the sheath by pushing the wire until the inflatable portion of the second balloon catheter is positioned across the stenosis and within the expandable portion of the sheath.

7. The method of claim 2, further comprising the step of inflating the expandable portion of the sheath after the step of removing the stiffening wire from the sheath and before the step of advancing the balloon catheter.

8. The method of claim 1, wherein the method is performed without contaminating the balloon catheter with the patient's bodily fluid.

9. The method of claim 1, wherein the step of advancing the balloon is performed without the balloon contacting the patient's circulatory system.

10. The method of claim 5, wherein the steps of removing the stiffening wire and loading a second stiffening wire is performed without the wire contacting the patient's circulatory system.

11. A stenosis dilatation method, comprising the steps of:
    inserting a sheath into a patient's circulatory system;
    positioning an expandable portion of the sheath across a stenosis;

loading one of a stiffening wire and another wire into a dilatation catheter;

advancing the loaded dilatation catheter through the sheath until an inflatable portion of the dilatation catheter is positioned across the stenosis and within the expandable portion of the sheath; and inflating the inflatable portion of the dilatation catheter, causing the expandable portion of the sheath to expand, thereby dilatating the stenosis.

12. The method of claim 11, wherein the method is performed without contaminating the dilatation catheter with the patient's bodily fluids.

13. The method of claim 11, further comprising the step of deflating the inflatable portion of the dilatation catheter to permit the expandable portion of the sheath to contract.

14. A stenosis dilatation method, comprising the steps of:

providing a sheath with a removable stiffening wire;

inserting the sheath and removable stiffening wire into a patient's circulatory system;

positioning an expandable portion of the sheath across a stenosis;

using the stiffening wire to advance and steer the sheath through the patient's circulatory system;

advancing a dilatation catheter through the sheath until an inflatable portion of the dilatation catheter is positioned across the stenosis and within the expandable portion of the sheath; and inflating the inflatable portion of the dilatation catheter, causing the expandable portion of the sheath to expand, thereby dilatating the stenosis.

15. The method of claim 14, wherein the step of using the stiffening wire to advance and steer the sheath further comprises the steps of:

determining that a different stiffening wire is desired;

removing the stiffening wire from the sheath; and loading a second stiffening wire into the sheath, all while the sheath remains within the patient's circulatory system.

16. The method of claim 14, further comprising the step of:

removing the stiffening wire from the sheath prior to advancing the dilatation catheter through the sheath.

17. The method of claim 14, wherein the step of advancing the dilatation catheter comprises pushing the dilatation catheter over the removable stiffening wire.

18. A stenosis dilatation method for reducing patient discomfort during prolonged dilatations, comprising the steps of:

preloading a slidably mounted perfusion device onto a sheath, the perfusion device having at least one perfusion tube of a length greater than an expandable portion of the sheath;

providing the sheath with a removable stiffening wire;

inserting the sheath, removable stiffening wire, and the preloaded perfusion device into a patient's circulatory system;

using the removable stiffening wire to advance and steer the sheath through the patient's circulatory system;

positioning the expandable portion of the sheath across a stenosis and the perfusion device proximal to the expandable portion of the sheath;

advancing a dilatation catheter through the sheath until an inflatable portion of the dilatation catheter is positioned across the stenosis and within the expandable portion of the sheath;

predilating the stenosis to a size sufficient to accommodate the perfusion device;

positioning the perfusion device across the dilatated stenosis such that one end of the perfusion tube is located distal to the expandable portion and another end is located proximal to the expandable portion; and inflating the inflatable portion of the dilatation catheter within the expandable portion of the sheath, whereby the patient's bodily fluids perfuse through the perfusion tube while the dilatation catheter remains inflated.

19. The method of claim 18, wherein the step of predilating is by inflating the inflatable portion of the dilatation catheter within the expandable portion of the sheath.

20. The method of claim 18, wherein the inflatable portion of the dilatation catheter is deflated prior to positioning the perfusion device across the dilatated stenosis.

21. The method of claim 18, wherein the method is performed without contaminating the dilatation catheter with the patient's bodily fluids.

* * * * *